(12) United States Patent
Metzner et al.

(10) Patent No.: US 7,045,601 B2
(45) Date of Patent: May 16, 2006

(54) STORAGE-STABLE, LIQUID FIBRINOGEN FORMULATION

(75) Inventors: Hubert Metzner, Marburg (DE); Uwe Liebing, Coelbe (DE); Gerhardt Kumpe, Wetter (DE); Stefan Schulte, Marburg (DE); Volker Gawantka, Lahntal (DE); Karlheinz Enssle, Marburg (DE)

(73) Assignee: ZLB BEHRING GmbH, Marburg (DE)

( * ) Notice: Subject to any disclaimer, the term of this patent is extended or adjusted under 35 U.S.C. 154(b) by 0 days.

(21) Appl. No.: 10/636,542

(22) Filed: Aug. 8, 2003

(65) Prior Publication Data

US 2005/0080009 A1 Apr. 14, 2005

(30) Foreign Application Priority Data

Aug. 13, 2002 (DE) .............................. 102 37 643
Dec. 20, 2002 (DE) .............................. 102 61 126

(51) Int. Cl.
*A61K 35/14* (2006.01)
*A61K 38/00* (2006.01)
*C12N 9/64* (2006.01)

(52) U.S. Cl. .................... 530/382; 530/380; 514/21; 514/12; 435/226

(58) Field of Classification Search ......... 530/380–386
See application file for complete search history.

(56) References Cited

U.S. PATENT DOCUMENTS

| | | | |
|---|---|---|---|
| 4,960,757 A | 10/1990 | Kumpe et al. | 514/21 |
| 5,099,003 A | 3/1992 | Kotitschke et al. | 530/382 |
| 5,407,671 A | 4/1995 | Heimburger et al. | 424/94.1 |
| 5,411,885 A | 5/1995 | Marx | 435/240.2 |
| 5,639,940 A | 6/1997 | Garner et al. | 800/2 |
| 5,925,738 A | 7/1999 | Miekka et al. | 530/380 |
| 5,962,405 A | 10/1999 | Seelich | 514/2 |
| 6,277,961 B1 * | 8/2001 | Hock et al. | 530/382 |
| 2001/0033837 A1 | 10/2001 | Metzner et al. | 424/94.3 |

FOREIGN PATENT DOCUMENTS

| | | |
|---|---|---|
| DE | 37 34 923 | 1/1989 |
| DE | 693 03 941 | 3/1994 |
| DE | 100 12 732 A1 | 9/2001 |
| EP | 0 103 196 | 3/1984 |
| EP | 0 253 198 | 1/1988 |
| EP | 0 804 933 A2 | 11/1997 |
| WO | WO 95/23868 | 9/1995 |
| WO | WO 96/30041 | 10/1996 |
| WO | WO 99/56797 | 11/1999 |
| WO | WO 01/48016 | 7/2001 |

OTHER PUBLICATIONS

Chabbat, J., Tellier, M., Porte, P., and Steinbuch, M. (1994) *Thrombosis Research* 76(6): 525-533.*
Beriplast® P, Combi-Set 1 ml Package Insert.
Janssen, C. et al., "Conditions for Stabilization and Determination of Activated Factor V," *Thrombosis Research*, 5:315-325 (1974).
Takebe, M. et al., "Calcium Ion-Dependent Monoclonal Antibody Against Human Fibrinogen: Preparation, Characterization, and Application to Fibrinogen Purification," *Thrombosis and Haemostasis*, 73(4):662-667 (1995).
Clauss, "Gerinnungsphysiologische Schnellmethode zur Bestimmung des Fibrinogens," *Acta Haemat.* 17:237-246 (1957). (English Abstract).

* cited by examiner

*Primary Examiner*—Karen Cochrane Carlson
*Assistant Examiner*—Marsha Tsay
(74) *Attorney, Agent, or Firm*—Finnegan, Henderson, Farabow, Garrett, & Dunner, L.L.P.

(57) ABSTRACT

The present invention relates to a novel storage-stable formulation for fibrinogen in liquid or viscous liquid form comprising divalent metal ions. The fibrinogen formulation may comprise other conventional formulation ingredients and particularly preferably comprises a complexing agent. The invention further relates to the production and use of the fibrinogen formulation of the invention.

34 Claims, No Drawings

STORAGE-STABLE, LIQUID FIBRINOGEN FORMULATION

CROSS REFERENCE TO RELATED APPLICATIONS

This application claims priority to German Patent Application No. 102 61 126.2 filed Dec. 20, 2002 and German Patent Application No. 102 37 643.3 filed Aug. 13, 2002.

The present invention relates to a novel storage-stable formulation for fibrinogen in liquid or viscous liquid form comprising divalent metal ions. The fibrinogen formulation may comprise other conventional formulation ingredients and particularly preferably comprises a complexing agent. The invention further relates to the production and use of the fibrinogen formulation of the invention.

Fibrinogen is a protein which is mainly produced in the liver and accounts for about 2–3% of the protein content of the plasma. It plays a key part in coagulation. Blood vessels are almost always damaged during injuries or operations, and hemorrhages arise. Blood is solidified by coagulation in the region of minor wounds, and the bleeding stops. The coagulation system thus protects the body from large blood losses. During coagulation, the soluble fibrinogen present in the plasma is converted into the fibrous insoluble fibrin and thus the thrombus acquires its eventual stability. The conversion of fibrinogen into fibrin takes place in the presence of thrombin. Thrombin is released in the blood in the event of injuries via a complicated chain reaction system involving many different coagulation factors.

Because of its importance for hemostasis and wound healing, fibrinogen is very important in clinical use.

Coagulation functions incorrectly if fibrinogen is lacking. The deficiency can be compensated by administering fibrinogen, e.g. isolated from human plasma. The fibrinogen deficiency may be caused for example by large-area wounds (e.g. severe burns), disseminated intravascular coagulation or serious hemorrhages. Fibrinogen is also very important as component of a fibrin sealant, in which case fibrinogen is usually converted into fibrin by adding a calcium-containing thrombin solution. A sealant of this type is employed for example for securing or sealing sutures, preferably in surgical interventions. It can also be employed advantageously for achieving hemostasis or sealing in particular on soft-tissue organs such as liver and spleen.

The stability of proteins is a general problem in the pharmaceutical industry and requires a new solution in detail for each protein. Depending on the protein, individual formulation ingredients may have a great influence on the stability, and the formulation ingredients may also depend on the planned storage form and storage temperature.

Proteins are frequently lyophilized with addition of certain excipients and stored in dry form. In these cases, a loss of stability during drying must be avoided as far as possible, and no loss of activity should occur on reconstitution either. Possible problems associated with reconstitution are, for example, flocculation or cloudiness, or long times until the protein has completely dissolved, especially at high protein concentrations. It is therefore advantageous if this step can be avoided. The freezing of protein samples, which is a frequently used alternative, has the disadvantage that the thawing and warming takes time, storage temperatures below 0° C. must be ensured, and multiple freezing and thawing is usually associated with losses of activity.

Accordingly, a great advantage for storage in liquid form generally and especially also for fibrinogen formulation is the possibility of immediate use of the active ingredient on the patient, because the time taken for reconstituting lyophilized formulations or the thawing and warming of frozen formulations becomes unnecessary. However, even with an intermediate storage as lyophilizate or in the frozen state it is advantageous for the reconstituted or thawed fibrinogen formulation, which is then in liquid form, to be stable for longer. This is evident for example in situations where, for example, material has been reconstituted as a precaution for operations but use was then unnecessary owing to medical considerations. If stability is only short-term, this material would have to be discarded and could not be used at a later date. However, a stability-related loss of material must be avoided especially in the case of therapeutic substances derived from human donors, because these are available only in limited quantities. Fibrinogen is one of these substances because it is obtained mainly from human plasma.

On use of fibrin sealants it is advantageous in particular for fibrinogen to be present in liquid form. The commercially available sealants usually comprise two components. One component comprises fibrinogen, frequently together with factor XIII and aprotinin, and the other component comprises thrombin, frequently together with calcium ions. Reconstitution to a sealant ready for use takes a relatively long time, especially since fibrinogen is present in high concentrations. However, the disadvantage of preparing the sealant as a precaution is that the efficacy of the sealant deteriorates or it even becomes completely useless, even if the thrombin-containing solution remains stable.

A further great advantage of the fibrinogen formulation of the invention in liquid or viscous liquid form is the resistance to aging, whereby the possibility of storage for a particular time even at room temperature and thus the use properties in emergency situations can be improved. It is also advantageous on lengthy transport routes where low temperatures cannot be ensured throughout for the stability to be ensured over a lengthy period even at room temperature. In rare cases of chronic fibrinogen deficiency (e.g. in cases of inherited impairment of fibrinogen synthesis) it may also be advantageous if continuous supply of fibrinogen to the patient is possible, the precondition for which is for the fibrinogen solution to be carried near the body, corresponding to a storage temperature of about 30° C. Stable liquid formulations of fibrinogen thus in many respects facilitate the production, the use, transport and administration to the patient.

There are publications on plasma proteins/coagulation factors which show that, besides other ingredients, calcium can also be used in liquid formulations. Reference may be made in this connection for example to WO 96/30041 and U.S. Pat. No. 5,925,738, where stability investigations were carried out on liquid formulations of factor VIII and/or FIX. Reduced activities of factor VIII and FIX respectively cause hemophilia A and B. For factor VIII for example the association of the heavy and light chains depends on divalent ions such as calcium. Data obtained for these factors are, however, not obviously applicable to fibrinogen, which is completely different both structurally and functionally. Fibrinogen is a very large protein with a complicated structure. It is a glycoprotein of about 340 kDa which consists of two symmetric halves. Pairs of alpha, beta and gamma chains are present in an elongate shape (about 47 nm) which forms three domains (a central E domain and two identical D domains). This complicated structure is indispensable for the formation of fibrin. Fibrinogen is, as substrate, the precursor for fibrin which forms a structural matrix. In contrast thereto, coagulation factors such as, for example, factor VIII and factor IX are, in their activated form, enzymes or cofactors which in turn activate other factors involved in the chain reaction for the formation of thrombin (FX), or speed up the activation thereof. When fibrinogen is stored it is necessary to ensure not only that the complicated structure is retained but also that fibrinogen does not associate to give covalently crosslinked, fibrin-like structures. In addition, in the prior art the combination of fibrinogen with calcium is avoided as far as possible on prolonged storage of fibrinogen concentrates in the liquid state. This is evident for example with the commercially available fibrin sealants. In these, the calcium necessary for the formation of crosslinked, stable fibrin is added for storage to the thrombin component, or is kept separate from both components but is not combined with the fibrinogen component. In the case of a single-component sealant with the ingredients fibrinogen, FXIII, prothrombin factors, a thrombin inhibitor and plasma inhibitor, which was developed from practical handling considerations in EP 0 253 198, the optimal calcium ion concentration is set only in relation to the activation of thrombin and is only 0.5–1 mM in the solution for use. Nowhere is it mentioned that calcium ions exert a stabilizing effect against non-proteolytic inactivation of fibrinogen. In addition, the mixture of the active ingredients for the sealant is preferably in solid form, such as preferably a lyophilizate. The fibrinogen formulations described and claimed therein do not, however, contain any significant amounts of prothrombin factors or thrombin.

Avoidance of simultaneous prolonged storage of fibrinogen and calcium ions in the liquid state is also evident in the cases where human plasma or fractions thereof used for obtaining fibrinogen are mixed inter alia with calcium ions for the heat treatment (pasteurization). The subsequent processing steps such as diafiltration or precipitation reduce the calcium concentration again, so that the amounts of calcium ions present in the final fibrinogen formulation are virtually negligible, e.g. about 1 mmol/l or less. Reference may be made in this connection to EP 0 103 196 in which 5 mM $CaCl_2$ is used during the pasteurization step but the concentration is then reduced again both in the formulation for intravenous infusion and in the formulation for producing fibrin sealants. Solution ingredients used for a treatment at high temperature over a short period (pasteurization) are of course not also automatically usable in solutions which are to be stored at low temperature or room temperature for several months or even years.

Finally, the patent application WO 01/48016 has disclosed a method for purifying fibrinogen in which fibrinogen is dissolved from the fraction I precipitate with an extraction buffer which may contain calcium ions. In the described steps of the method there is elimination of plasminogen impurities which may result in proteolytic inactivation of fibrinogen. There has been no report to date of stabilization of fibrinogen by divalent metal ions in relation to non-proteolytic inactivation during storage.

It has been possible to show with the present invention, surprisingly, that the non-proteolytic inactivation of fibrinogen during prolonged storage in liquid form in the temperature range 0–30° C. can be prevented or reduced by adding divalent metal ions. It was surprisingly possible to achieve further increases in the stability by simultaneous use of complexing agents. The fibrinogen product of the invention is stable in the liquid state and moreover substantially free of covalent fibrinogen aggregates having more than five fibrinogen molecules.

The object on which the present invention is based is thus to provide a storage-stable fibrinogen formulation which is stable for at least one month on storage in the liquid or viscous liquid state in the temperature range 0–30° C., preferably 2–8° C. This object is achieved by a formulation which, besides fibrinogen, comprises divalent metal ions in a concentration of up to 100 mM and, where appropriate, one or more further formulation ingredients. Further embodiments relate to the subject matter of claims 2 to 29 and further features and advantages of the invention are evident from the description of the preferred embodiments and the examples.

The present invention encompasses a formulation for fibrinogen (fibrinogen formulation) which is stable for at least one month in the liquid or viscous liquid state in the temperature range 0–30° C., preferably 2–8° C., through the addition of divalent metal ions and, where appropriate, one or more further formulation ingredients. The term "stable" for the purposes of the present invention means that no substantial loss of activity due to non-proteolytic inactivation occurs on storage of the fibrinogen formulation, but at least 70% of the initial activity is retained. The loss of activity is to be determined in this connection preferably by the method for determining clottable protein as described in the fibrin sealant monograph of the European Pharmacopoeia (3rd edition (1997), pages 944–946). The storage temperature is in the range 0–30° C., preferably 2 to 10° C. and particularly preferably 2–8° C. Positive stabilizing effects on the fibrinogen formulation are also to be expected at storage temperatures in the region of body temperature (37° C.). A particularly preferred fibrinogen formulation is stable for more than 3, and in particular more than 6, months. In a particularly preferred embodiment, the fibrinogen formulation of the invention is stable for 24 months or more. The fibrinogen formulation of the invention can thus preferably be employed where prolonged storage in the liquid or viscous liquid state of one month and more is desired.

The term fibrinogen preferably means human fibrinogen which has been obtained for example from human plasma. It can moreover be isolated both from pooled plasma donations and from individual donations. However, fibrinogen isolated from plasma or milk of animals such as, preferably, mammals (e.g. pigs, horses, cattle, goats, sheep and dogs) is also encompassed. If fibrinogen is isolated and/or purified from plasma, there is usually simultaneous purification of further plasma proteins such as, in particular, factor XIII (F XIII). Further co-isolated plasma proteins may be for example, depending on their mode of purification, fibronectin, coagulation factors, von Willebrand factor, serum albumin and/or growth factors. Besides fibrinogen as main ingredient, the fibrinogen formulation of the invention may thus also comprise further plasma proteins. An example thereof is factor XIII. FXIII is converted by thrombin into the activated form and is capable of covalent linkage of the polymerized fibrin molecules. This is advantageous in particular when the fibrinogen formulation is used for fibrin sealants.

However the term fibrinogen used for the fibrinogen formulation of the invention also encompasses fibrinogen or active fibrinogen derivatives produced by recombinant methods. A preferred recombinant possibility for producing human fibrinogen is from body fluids, in particular the milk, of transgenic animals. For known techniques in this connection, reference may be made for example to U.S. Pat. No. 5,639,940 and WO 95/23868. Recombinantly produced fibrinogen can also be mixed in the fibrinogen formulation of the invention for applications such as, for example, the fibrin sealant with further proteins, in particular FXIII in order to alter the constitution of the sealant (see, for example, WO 99/56797) or may contain additions which are intended for slow release.

If the fibrinogen used in the fibrinogen formulation is isolated from transgenic/recombinant production, plasma and, in particular, from human plasma, the fibrinogen used is preferably subjected to one or more virus inactivation or virus reduction methods. These comprise conventional methods such as, for example, pasteurization, heating in the dry state with exclusion of oxygen, nanofiltration, chemical additions (for example detergents), UV irradiation or combinations thereof.

Fibrinogen is present in the fibrinogen formulation preferably as monomeric unit, but multimeric units are also possible but preferably do not adversely affect the product properties. The intention in particular of the choice of the formulation ingredients and the ratio of complexing agent to divalent metal ions is to avoid the formation of covalently linked aggregates with more than five fibrinogen molecules during storage.

The term "liquid" encompasses for the purposes of the present invention preferably aqueous solutions, i.e. solutions which necessarily also contain water. However, "nonaqueous" solutions are also encompassed, such as, for example, dimethyl sulfoxide, glycerol, polyethylene glycol and polypropylene glycol or mixtures thereof. Also encompassed are aqueous solutions which are combined with "nonaqueous" solutions. The term "viscous liquid" encompasses liquid solutions which are viscous because of physical or biochemical changes or because of formulation ingredients such as, for example, hyaluronic acids. Nonaqueous suspensions such as, for example, alcoholic suspensions are also encompassed.

The fibrinogen can be stored immediately after production in the liquid fibrinogen formulation of the invention or else undergo intermediate storage as lyophilizate or in the frozen state. The fibrinogen formulation of the invention in the liquid state can be employed on the patient directly.

The divalent metal ions in the fibrinogen formulation of the invention can be, for example, alkaline earth metals such as, for example, magnesium and calcium ions, or elements of non-main groups such as, for example, zinc or manganese ions. Calcium and zinc ions are particularly preferred and can be added for example in the form of $CaCl_2$ and $ZnCl_2$. The divalent ions which are suitable in principle are those which increase the stability of fibrinogen but cause negligible adverse side effects on administration to the patient in the concentration used. The concentration of the divalent metal ions is in the range up to 100 mM, preferably in the range up to 40 mM and particularly preferably between 0.02 and 10 mM. The preferred concentrations should be chosen depending on the divalent ions used. Thus, the particularly preferred concentration of calcium ions for example is in the range from about 1.5 to 10 mM, whereas for zinc ions the particularly preferred concentration is in the range from 0.02 to 1.5 mM.

A further advantageous formulation ingredient is in a preferred embodiment of the fibrinogen formulation of the invention a complexing agent. This complexing agent is able to bind divalent ions such as, for example, calcium ions. It has surprisingly been possible to show within the scope of this invention that the stability of the liquid fibrinogen formulation can be increased further through addition of such a complexing agent, although it is to be expected that a considerable proportion of the stabilizing divalent ions is present in complexed form in the presence of a complexing agent. Examples of possible complexing agents are citrate, oxalate and EDTA (ethylenediaminetetraacetic acid). Particular preference is given in this connection to citrate, which can be added for example as sodium citrate. The complexing agent is preferably present in the formulation of the invention in a higher concentration than the divalent metal ions. The complexing agent can be present in concentrations up to 150 mM, but preferably up to 50 mM and particularly preferably up to 25 mM.

The fibrinogen formulation of the invention may comprise further conventional formulation ingredients such as, for example, monovalent metal salts, amino acids, lyophilization auxiliaries, carbohydrates, detergents, chaotropic agents, inhibitors such as fibrinolysis or fibrinogenolysis inhibitors, protease inhibitors, plasma proteins, antioxidants, buffer substances or mixtures thereof. These additions are substantially known to the skilled worker and are to be selected on the basis of various requirements. Additions may be selected for example depending on a planned intermediate storage (lyophilizate, frozen state). Known lyophilization auxiliaries for proteins are, for example, saccharides such as sucrose and dextran, sugar alcohols such as, for example, mannitol and sorbitol or amino acids. The planned use of the formulation is, of course, also decisive for the particular formulation. The additions known to the skilled worker which are advisable for an intravenous administration of fibrinogen may be different from those for use as fibrin sealant.

Suitable monovalent metal salts are some alkali metal salts known to the skilled worker, with preference for sodium and potassium salts or mixtures thereof. Sodium ions are particularly preferred and may be present in the form of, for example, sodium chloride. The concentration of the monovalent metal salts is preferably ≦300 mM. In a particularly preferred embodiment, the concentration is ≦200 mM.

The term amino acid encompasses both naturally occurring amino acids and derivatives thereof. Particularly preferred examples are neutral amino acids such as glycine and the acidic or basic amino acids (aspartic acid, glutamic acid, and histidine, lysine, arginine) or mixtures thereof. Arginine or mixtures including arginine are particularly preferably employed. However, amino acid derivatives such as, for example, citrulline can also be employed.

Possible inhibitors include proteinase inhibitors which are to be chosen from conventional substances, and aprotinin or inhibitors of similar specificity are preferably used.

Fibrinolysis inhibitors include, for example, antiplasmins, encompassing α-2-antiplasmin, α-2-macroglobulin, α-1-antiplasmin, plasminogen activator inhibitors (PAI), comprising PAI-1 and PAI-2, thrombin-activatable fibrinolysis inhibitor (TAFI), aprotinin and/or synthetic substances such as ε-aminocaproic acid or p-aminomethylbenzoic acid. Fibrinolysis inhibitors are of interest in particular in applications where resulting fibrin polymers are to be stable for as long as possible.

Fibrinogenolysis inhibitors which can be employed are, for example, antiplasmins, C1 inhibitor and antithrombin, with antithrombin preferably being used in the presence of heparin.

The plasma proteins may be, as already mentioned, coagulation factors such as, for example, F XIII or proteins such as, for example, fibronectin, von Willebrand factor, serum albumin or growth factors. They may already be present as contaminating proteins in the isolated fibrinogen or may be added subsequently to the fibrinogen formulation. The plasma proteins should not, however, include thrombin because simultaneous storage of fibrinogen and thrombin may lead to fibrin formation, and the stability of the fibrinogen formulation cannot be ensured.

Carbohydrates include, for example, glucose, fructose, sucrose, maltose, mannose, trehalose, lactose, cellulose and starch or derivatives thereof. Also in the form of mixtures. Also encompassed are sugar alcohols such as sorbitol and mannitol. Carbohydrates also mean for the purposes of the invention heteropolysaccharides. These include, for example, glycosaminoglycans such as, in particular, hyaluronic acid.

Detergents likewise include conventional substances, but preferably nonionic detergents such as, for example, poloxamers or polysorbates.

Chaotropic agents mean agents able to break hydrogen bonds. Particular preference is given to urea and guanidine or guanidino group-containing additions, and related compounds or mixtures thereof or chaotropic salts such as, for example, KI.

Antioxidants which can be used are conventional substances and preferably ascorbic acid.

Buffer substances are substances which adjust and keep substantially constant the pH of the fibrinogen formulation. In the preferred embodiments, the pH of the formulation is adjusted to a value between 5.0 and 8.0, more preferably between 6.0 and 8.0, and the pH is particularly preferably between 6.5 and 7.5. Examples of possible buffer substances of this type are amino acids and/or citrate, and in a particularly preferred embodiment citrate. Other conventional buffer systems such as, for example, tris(hydroxymethyl)aminomethane, phosphate, acetate, succinate, glycylglycine, carbonate and bicarbonate are likewise encompassed. The adjustment or correction of the pH can take place by acids or bases such as, for example, HCl and NaOH.

It applies to all formulation ingredients which can be used that they must not cause any substantial adverse side effects in the patient in the amount used.

In a particularly preferred embodiment, a fibrinogen formulation of the invention comprises besides calcium chloride and sodium citrate for example also sodium chloride and arginine. In a further preferred formulation, aprotinin or C1 inhibitor is also present in addition to calcium chloride, sodium citrate, sodium chloride and arginine.

Further particularly preferred fibrinogen formulations are evident from the examples.

The invention further relates to a process for producing the fibrinogen formulation of the invention. This entails fibrinogen firstly being obtained (isolated and/or purified) by methods known to the skilled worker. It is preferably obtained from human plasma, but obtaining from animal plasma is also possible. Recombinant fibrinogen can be obtained for example from the fermentation supernatant of animal cell cultures or the milk of transgenic animals. If the obtained fibrinogen is initially present in a solution which does not correspond to the fibrinogen formulation of the invention, this is replaced by a solution which comprises the formulation ingredients of the invention described in the embodiments, in particular divalent metal ions. Exchange or assimilation of different solutions is possible for example by methods such as ultrafiltration, dialysis, dilutions or addition of missing formulation ingredients. If fibrinogen has been precipitated by known precipitation methods (e.g. with ethanol, polyethylene glycol, ammonium sulfate, glycine), it can be resuspended or dissolved in a solution containing the divalent ions of the invention and further formulation ingredients. If fibrinogen is in the form of a lyophilizate, it can be reconstituted in a solution so that the resulting formulation corresponds to the fibrinogen formulation of the invention.

The fibrinogen formulation of the invention obtained in this way can be stored directly in the liquid state. Alternatively, the liquid formulation can also be subjected to intermediate freezing or lyophilization and, after thawing or reconstitution, be stored further in the liquid state corresponding to a fibrinogen formulation of the invention.

A particularly preferred production of the fibrinogen formulation of the invention takes place with fibrinogen which is obtained from human plasma and comprises the following main steps:

production of a crude plasma fraction adsorption onto aluminum hydroxide virus inactivation precipitation further purification and/or virus inactivation steps replacement of solution components by a solution comprising at least one divalent metal salt, and further formulation ingredients, pH adjustment and concentration adjustment by ultrafiltration, dialysis and/or dilution sterilization by filtration storage of the fibrinogen formulation directly in the liquid state or intermediate freezing or lyophilization with subsequent storage in the liquid state through thawing or reconstitution.

The invention further relates to the use of the fibrinogen formulation of the invention. Possible applications are known to the skilled worker, and the fibrinogen formulation of the invention can be employed for all known uses of fibrinogen. The fibrinogen formulation of the invention is generally suitable for the therapy of fibrinogen deficiency states. These deficiency states may occur for example in cases of major wounds and after severe hemorrhages, in cases of large-area burns, pathological activation of hemostasis (consumption coagulopathy, also called DIC (disseminated intravascular coagulation)), through medicaments or severe liver disorders (e.g. when synthesis is impaired due to liver parenchymal damage). Besides the described acquired hypofibrinogenemias (reduced fibrinogen in the blood) and afibrinogenemias (lack or greatly reduced fibrinogen in the blood) there are also rare cases of an inherited afibrinogenemia or hypofibrinogenemia which may be caused by absent or reduced fibrinogen synthesis in the liver.

In cases of hypofibrinogenamia and afibrinogenemia, the fibrinogen formulation of the invention is preferably injected intravenously into the patient in order to compensate corresponding fibrinogen deficiency states. Dosages are based on the level of deficiency occurring.

Fibrinogen has great importance in fibrin therapy as important component of so-called fibrin sealants. A fibrin sealant simulates the last step of coagulation through the formation of crosslinked fibrin on combination of fibrinogen with thrombin in the presence of calcium and FXIII.

There are diverse possible applications of fibrin sealants in medicine. Important ones to mention are hemostasis, wound closure, adhesion prophylaxis and wound healing. Local intraoperative hemostasis is particularly important on parenchymal organs and in the cardiovascular area. Even severe hemorrhages after serious liver injury can be controlled in this way. Fibrin sealants are also employed for the closure and fixation of skin wounds (including skin transplant) and for sealing sutures (e.g. on the duodenal stump). Examples which may also be mentioned are the use in duraplasty and for cavity obliteration, and for adhesion of the pleural membranes for palliative treatment of pleural effusions. The fibrin sealants can also be employed advantageously for bonding connective tissues such as bones, cartilage and tendons.

Fibrinogen can also be used as a component for producing a fibrin matrix. A carrier material of this type can be used for slow release of active ingredients such as, for example, growth factors (e.g. with osteoinductive proteins as matrix for bone regeneration), antibiotics, antiinflammatory, cytostatic or wound healing-promoting additions. The carrier may also consist of a mixture of fibrin with other materials.

A fibrin matrix additionally has extensive possible uses in biotechnology, such as, for example, as support material and culture medium for cells and tissues in tissue engineering or for enveloping implants such as, for example, biosensors.

The invention is additionally to be illustrated by the following examples which, however, are not intended to have any restrictive effect.

EXAMPLE 1

Production of Fibrinogen from Human Plasma

To obtain fibrinogen starting material, cryoprecipitate was dissolved in NaCl/glycine solution, and an adsorption was carried out with 10% (v/v) aluminum hydroxide suspension (Al(OH)$_3$). After the Al(OH)$_3$ had been removed by centrifugation, the remaining supernatant was precipitated with glycine (final concentration 2.45 M). For further processing, the fibrinogen-rich precipitate was dissolved in NaCl solution, and the pH of the solution was adjusted to 7.3. The fibrinogen solution was adsorbed with 80 ml of aluminum hydroxide suspension per liter of solution. The Al(OH)$_3$ was then removed by filtration or centrifugation and discarded. For the subsequent pasteurization, the fibrinogen solution was diluted with physiological NaCl solution to $OD_{280-320\,nm}$=48. The solution was stirred while 0.37 g of calcium chloride dihydrate, 1 000 g of sucrose and 75 g of glycine were added per liter of solution. The pH was kept at pH 7.5.

The solution was then heated to +60° C., and the temperature was kept constant for 10 h. The solution was then cooled.

The fibrinogen solution which was now pasteurized was mixed with three times the volume of diluent solution (3.5 g/l NaCl; 6 g/l trisodium citrate dihydrate in water). 90 g of glycine were added with stirring per liter of diluted solution. The resulting precipitate was removed by centrifugation or filtration and discarded.

A further 75 g of glycine was added per liter to the supernatant. The fibrinogen-rich precipitate was obtained by centrifugation and stored at −25° C. until processed further.

For further purification and removal of plasminogen, the fibrinogen-rich precipitate was initially dissolved in a suitable aqueous solvent (50 mM NaCl; 20 mM trisodium citrate dihydrate) and, preferably after dialysis against the solvent, pumped through a chromatography column with a matrix carrying L-lysyl radicals as ligands.

Fibrinogen formulations were produced by initially adjusting the fibrinogen-containing solution by means of suitable ultrafiltration methods to a protein concentration of about $OD_{280-320\,nm}$=2–200, preferably about 20–160, depending on the use, and subsequently dialyzing against solutions containing the formulation ingredients specified in example 2.

Sterilization by filtration results in fibrinogen formulations which were tested for stability in accordance with the following examples.

EXAMPLE 2

Stability Investigations on Fibrinogen Formulations

The stability of fibrinogen in various formulations was investigated by using human fibrinogen produced as described in example 1. For this purpose, containers with fibrinogen solutions ($OD_{280-320\,nm}$=about 100) in various formulations were stored at either 30° C. or 2–8° C. for various storage periods (0, 1, 2, 3 and/or more months). After the appropriate storage periods, the remaining content of fibrinogen was determined. For this purpose, the content of clottable protein was determined as described in the fibrin sealant monograph of the European Pharmacopoeia (3rd edition (1997), pages 944–946).

In the three formulations detailed below, besides 200 mM NaCl and 10% L-ArgxHCl, at a pH of 7.2 either sodium citrate or calcium chloride or sodium citrate combined with calcium chloride were added.

Formulation 1: 20 mM Na$_3$ citrate/200 mM NaCl/10% L-ArgxHCl/pH 7.2

Formulation 2: 2.5 mM CaCl$_2$/200 mM NaCl/10% L-Argx HCl/pH 7.2

Formulation 3: 20 mM Na$_3$ citrate/2.5 mM CaCl$_2$/200 mM NaCl/10% L-ArgxHCl/pH 7.2

TABLE 1

Clottable protein, storage at 30° C.

| | Storage time | | | |
|---|---|---|---|---|
| | 0 | 1 month | 2 months | 3 months |
| Formulation 1 | 100% | 93.1% | 46.1% | 28.9% |
| Formulation 2 | 100% | 93.5% | 79.6% | 61.9% |
| Formulation 3 | 100% | 99.7% | 101.6% | 92.6% |

TABLE 2

Clottable protein, storage at 2–8° C.

| | Storage time | | | |
|---|---|---|---|---|
| | 0 | 1 month | 3 months | 6 months |
| Formulation 1 | 100% | 110.8% | 99.4% | 91.6% |
| Formulation 3 | 100% | 110.9% | 106.2% | 97.5% |

The tests show unambiguously that addition of CaCl$_2$ (formulation 2) is able to achieve a marked stabilization of fibrinogen on storage at 30° C. compared with the control formulation with CaCl$_2$ (formulation 1). Even after storage for three months, the amount of clottable fibrinogen detectable is still more than twice that in the control formulation (table 1). The increase in stability is even more marked in the formulation which contains CaCl$_2$ combined with the complexing agent sodium citrate (formulation 3), which in fact still contains approximately three times as much clottable protein as in the control formulation 1 after storage at 30° C. for three months. The stabilizing effect of CaCl$_2$ and sodium citrate (formulation 3) is far less marked but still detectable by comparison with the control formulation on storage at 2–8° C. for 3 or 6 months (table 2). Since a better stability is generally to be expected on storage at 2–8° C., it is only to be expected that the difference may be less.

Further tests were carried out on various formulations in which the concentrations of the other formulation ingredients were reduced. The fibrinogen formulations used ($OD_{280-320\,nm}$=about 134 to 146) were produced in a manner comparable to that described in example 1 and were stored at 30° C. for various storage periods (0, 1, 2 and/or 3 months). After the appropriate storage periods, either the content of clottable protein (fibrin sealant monograph of the European Pharmacopoeia, 3rd edition 1997, pages 944–946) was determined, or fibrinogen was determined by the method of Clauss (Clauss (1957), Acta-Haematol. 17, 237–246) (table 3 and 4).

Formulation 4: 4 mM $Na_3$ citrate/100 mM NaCl/5% L-Arg×HCl/pH 7.2

Formulation 5: 4 mM $Na_3$ citrate/0.5 mM $CaCl_2$/100 mM NaCl/5% L-Arg×HCl/pH 7.2

Formulation 6: 20 mM $Na_3$ citrate/2.5 mM $CaCl_2$/100 mM NaCl/5% L-Arg×HCl/pH 7.2

Formulation 7: 12 mM $Na_3$ citrate/1.5 mM $CaCl_2$/100 mM NaCl/5% L-Arg×HCl/pH 7.2

TABLE 3

Clottable protein, storage at 30° C.

| | Storage time | | | |
|---|---|---|---|---|
| | 0 | 1 month | 2 months | 3 months |
| Formulation 4 | 100% | 104.6% | 73.9% | 46.7% |
| Formulation 5 | 100% | 112.5% | 95.5% | 91.9% |

TABLE 4

Fibrinogen by the method of Clauss, storage at 30° C.

| | Storage time | |
|---|---|---|
| | 0 | 1 month |
| Formulation 4 | 100% | 50.2% |
| Formulation 5 | 100% | 70.5% |
| Formulation 6 | 100% | 79.5% |
| Formulation 7 | 100% | 78.0% |

This test shows that a marked increase in stability compared with the control formulation (formulation 4) can be achieved in formulations 5 to 7 too as long as calcium chloride or calcium chloride and citrate are present. Moreover, according to the Clauss fibrinogen test, there is a trend for the effect to be even better for the higher concentrations of calcium chloride and citrate.

The invention claimed is:

1. A storage-stable, liquid or viscous liquid fibrinogen formulation, comprising fibrinogen, divalent metal ions in a concentration of up to 100 mM, and a complexing agent, wherein the fibrinogen formulation is stable at storage temperatures between 0° C. and 30° C. for at least 1 month.

2. The fibrinogen formulation as claimed in claim 1, wherein the divalent metal ions are calcium ions, zinc ions or mixtures of the two.

3. The fibrinogen formulation as claimed in claim 1, wherein the divalent metal ions are present in a concentration of up to 40 mM.

4. The fibrinogen formulation as claimed in claim 1, wherein the complexing agent is citrate.

5. The fibrinogen formulation as claimed in claim 1, wherein the complexing agent is present in a higher concentration than the divalent metal ions.

6. The fibrinogen formulation as claimed in claim 1, wherein the complexing agent is present in a concentration of up to 150 mM.

7. The fibrinogen formulation as claimed in claim 1, further comprising at least one of monovalent metal salts, amino acids, lyophilization auxiliaries, detergents, fibrinolysis inhibitors, fibrinogenolysis inhibitors, protease inhibitors, plasma proteins, carbohydrates, antioxidants, buffer substances or chaotropic agents.

8. The fibrinogen formulation as claimed in claim 7, wherein the plasma proteins comprise at least one of factor XIII, fibronectin, serum albumin, von Willebrand factor or growth factors.

9. The fibrinogen formulation as claimed in claim 7, further comprising calcium chloride, sodium citrate, sodium chloride and arginine.

10. The fibrinogen formulation as claimed in claim 9, further comprising at least one of aprotinin or C1 inhibitor.

11. The fibrinogen formulation as claimed in claim 9, further comprising albumin.

12. The fibrinogen formulation as claimed in claim 1, which has a pH of from 5.0 to 8.0.

13. The fibrinogen formulation as claimed in claim 12, which has a pH of from 6.5 to 7.5.

14. The fibrinogen formulation as claimed in claim 1, wherein the fibrinogen formulation is stable at from 0° C. to 30° C., over a period of at least 3 months.

15. The fibrinogen formulation as claimed in claim 14, where the fibrinogen formulation is stable over a period of at least 6 months.

16. The fibrinogen formulation as claimed in claim 14, where the fibrinogen formulation is stable over a period of at least 24 months.

17. The fibrinogen formulation as claimed in claim 1, wherein the fibrinogen has been subjected to at least one virus inactivation or virus reduction methods.

18. A process for producing the fibrinogen formulation as claimed in claim 1 comprising:
    (a) isolating fibrinogen, or a fragment thereof;
    (b) replacing the first solution containing the fibrinogen with a second solution comprising at least one divalent metal salt and and at least one complexing agent; and
    (c) adjusting the pH and the second solution concentration by at least one of ultrafiltration, dialysis or dilution.

19. The process for producing a fibrinogen formulation as claimed in claim 18, wherein the fibrinogen is recombinant.

20. The process for producing a fibrinogen formulation according to claim 18, wherein the fibrinogen is isolated from plasma.

21. The process for producing a fibrinogen formulation according to claim 20, wherein the fibrinogen is isolated from human plasma.

22. The process for producing a fibrinogen formulation as claimed in claim 18, further comprising storing the fibrinogen formulation in the form of a lyophilizate.

23. The process for producing a fibrinogen formulation as claimed in claim 18, further comprising freezing the fibrinogen formulation.

24. A method for producing a fibrinogen formulation as claimed in of claim 18 further comprising adding formulation ingredients, wherein the formulation ingredients are chosen from at least one of monovalent metal salts, amino acids, lyophilization auxiliaries, detergents, fibrinolysis inhibitors, fibrinogenolysis inhibitors, protease inhibitors, plasma proteins, carbohydrates, antioxidants, buffer substances, chaotropic agents, calcium chloride, sodium citrate, sodium chloride, arginine, aprotinin, C1 inhibitor, and albumin.

25. A method for producing a fibrinogen formulation as claimed in claim 22, further comprising reconstituting the lyophilized fibrinogen formulation in a solution.

26. A method for the treatment of fibrinogen deficiency states, comprising administering to a patient the fibrinogen formulation according to claim 1.

27. A method of a fibrin therapy, comprising administering to a patient a fibrin sealant, wherein the fibrin sealant comprises the fibrinogen formulation according to claim 1.

28. A method of a fibrin therapy, comprising administering to a patient a fibrin matrix, wherein the fibrin matrix comprises the fibrinogen formulation according to claim 1.

29. A method of diagnosing a fibrinogen deficiency state, comprising combining the fibrinogen formulation according to claim 1 with a biological sample.

30. The fibrinogen formulation as claimed in claim 12, which has a pH of from 6.0 to 8.0.

31. The fibrinogen formulation as claimed in claim 3, wherein the divalent metal ions are present in a concentration of from 0.02 mM to 10 mM.

32. The fibrinogen formulation as claimed in claim 6, wherein the complexing agent is present in a concentration of up to 50 mM.

33. The fibrinogen formulation as claimed in claim 6, wherein the complexing agent is present in a concentration of up to 20 mM.

34. The fibrinogen formulation as claimed in any one of claims 14–16, wherein the fibrinogen formulation is stable at from 2° C. to 8° C.

* * * * *